(12) United States Patent
Clark

(10) Patent No.: US 9,040,783 B2
(45) Date of Patent: May 26, 2015

(54) BARLEY CULTIVAR BG-161

(71) Applicant: Monsanto Technology LLC, St. Louis, MO (US)

(72) Inventor: Dale R. Clark, Bozeman, MT (US)

(73) Assignee: Monsanto Technology LLC, St. Louis, MI (US)

( * ) Notice: Subject to any disclaimer, the term of this patent is extended or adjusted under 35 U.S.C. 154(b) by 77 days.

(21) Appl. No.: 13/644,224

(22) Filed: Oct. 3, 2012

(65) Prior Publication Data

US 2014/0096279 A1    Apr. 3, 2014

(51) Int. Cl.
*A01H 5/10* (2006.01)
*C12N 15/82* (2006.01)

(52) U.S. Cl.
CPC ........ *C12N 15/8289* (2013.01); *C12N 15/8282* (2013.01); *C12N 15/8286* (2013.01); *C12N 15/8283* (2013.01); *C12N 15/8274* (2013.01); *C12N 15/8278* (2013.01); *C12N 15/8275* (2013.01); *C12N 15/8247* (2013.01); *C12N 15/8245* (2013.01); *C12N 15/8251* (2013.01); *C12N 15/8273* (2013.01); *A01H 5/10* (2013.01)

(58) Field of Classification Search
None
See application file for complete search history.

(56) References Cited

U.S. PATENT DOCUMENTS 7,897,851 B2 *   3/2011   Clark ............................ 800/320

* cited by examiner

*Primary Examiner* — Medina A Ibrahim
(74) *Attorney, Agent, or Firm* — Nelson Mullins Riley & Scarborough LLP

(57) ABSTRACT

A barley cultivar, designated BG-161, is disclosed. The invention relates to seeds, plants, and hybrids of barley cultivar BG-161, and methods for producing a barley plant produced by crossing plants from barley cultivar BG-161 with themselves or plants from another barley variety. The invention also relates to methods for producing a barley plant containing in its genetic material one or more transgenes and to the transgenic barley plants and plant parts produced by those methods. The invention also relates to barley varieties derived from barley cultivar BG-161, to methods for producing other barley varieties, lines or plant parts derived from barley cultivar BG-161, and to the barley plants, varieties, and their parts derived from the use of those methods. The invention further relates to hybrid barley seeds and plants produced by crossing barley cultivar BG-161 with another barley cultivar.

22 Claims, No Drawings

US 9,040,783 B2

BARLEY CULTIVAR BG-161

BACKGROUND OF THE INVENTION

Field of the Invention

The present invention relates generally to a new barley cultivar, designated as BG-161, as well as to seeds, plants, cultivars and hybrids related thereto. The invention also relates to methods for producing barley seeds and plants from BG-161.

SUMMARY OF THE INVENTION

In an embodiment, the invention is directed to a seed of barley cultivar BG-161, wherein a representative sample of seed was deposited under ATCC Accession No. PTA-121758. The invention is additionally directed, in various embodiments, to plants and hybrids of barley cultivar BG-161.

The invention is also directed, in embodiments, to a method of introducing a desired trait into barley cultivar BG-161 wherein the method comprises: crossing a BG-161 plant, wherein a representative sample of seed was deposited under ATCC Accession No. PTA-121758, with a plant of another barley cultivar that comprises a desired trait to produce progeny plants wherein the desired trait is selected from the group consisting of male sterility, herbicide resistance, insect resistance, modified fatty acid metabolism, modified carbohydrate metabolism, modified phytic acid metabolism, modified waxy starch content, modified protein content, increased stress to water tolerance and resistance to bacterial disease, fungal disease or viral disease; selecting one or more progeny plants that have the desired trait to produce selected progeny plants; crossing the selected progeny plants with the BG-161 plants to produce backcross progeny plants; selecting for backcross progeny plants that have the desired trait and essentially all of the physiological and morphological characteristics of barley cultivar BG-161 listed in Table 1 to produce selected backcross progeny plants; and repeating the crossing the selected progeny step and selecting for backcross progeny step two or more times in succession to produce selected third or higher backcross progeny plants that comprise the desired trait and essentially all of the physiological and morphological characteristics of barley cultivar BG-161 listed in Table 1.

DETAILED DESCRIPTION OF THE INVENTION

The following definitions apply to the terms used herein:

Allele. An allele is any of one or more alternative forms of a gene which relate to one trait or characteristic. In a diploid cell or organism, the two alleles of a given gene occupy corresponding loci on a pair of homologous chromosomes.

Awn. Awn is intended to mean the elongated needle-like appendages on the flower- and seed-bearing head at the top of the barley plant. Awns are attached to the lemmas, which enclose the stamen and the stigma as part of the florets.

Backcrossing. Backcrossing is a process in which a breeder repeatedly crosses hybrid progeny back to one of the parents, for example, a first generation hybrid $F_1$ with one of the parental genotypes of the $F_1$ hybrid.

Barley Yellow Dwarf Virus. Barley yellow dwarf virus is a viral disease transmitted by aphids. The symptoms include yellow chlorosis of the older leaves, stunting, sterility and reduced kernel size.

Beta-Glucan Fiber. Beta-glucan fiber is a nonstarch polysaccharide in which individual glucose molecules (20,000-1,000,000) are linked by beta 1-4 and beta 1-3 linkages. Beta-glucan is soluble in warm water (40-45 degrees Centigrade). Beta-glucan is the main structural material in the cell walls of barley and oat grain.

Beta-Glucan Fiber Viscosity. Beta-glucan fiber viscosity describes the friction that is created in a solution by the presence of beta-glucan chains (fibers) and is measured in centipoise units.

Cell. As used herein, the term cell includes a plant cell, whether isolated, in tissue culture, or incorporated in a plant or plant part.

Centipoise Units (cps). Centipoise units (cps) are the units commonly used to measure viscosity. By definition, the fundamental unit of viscosity measurement is the poise.

Covered Seed. A covered seed is a barley seed that has a cutin layer which cements the hull (lemma and palea or glumes) to the seed. This trait is controlled by the Nud locus on chromosome 1 (7H). The homozygous dominant Nud Nud genotype results in the presence of cutin and is referred to as covered. The hull can only be removed by abrasive processing prior to consumption, known as pearling.

Disease Resistance. As used herein, the term disease resistance or disease resistant is defined as the ability of plants to restrict the activities of a specified disease, such as a fungus, virus, or bacterium.

Disease Tolerance. As used herein, the term disease tolerance or disease tolerant is defined as the ability of plants to endure a specified disease (such as a fungus, virus or bacterium) or an adverse environmental condition and still perform and produce in spite of this condition.

Essentially all of the physiological and morphological characteristics. This phrase refers to a plant having essentially all of the physiological and morphological characteristics of the referenced plant or variety, as determined at a 5% significance level for quantitative data.

Foliar disease. Foliar disease is a general term for fungal disease which causes yellowing or browning or premature drying of the leaves. The disease typically involves *Septoria*, net blotch, spot blotch or scald.

Head. Interchangeable with the term spike, the term head refers to a group of spikelets at the top of one plant stem.

Herbicide Resistance. As used herein, the term herbicide resistance or herbicide resistant is defined as the ability of plants to survive and reproduce following exposure to a dose of herbicide that would normally be lethal to the plant.

Herbicide Tolerance. As used herein, the term herbicide tolerance or herbicide tolerant is defined as the ability of plants to survive and reproduce after herbicide treatment.

Homozygous Plant. The term homozygous plant is defined as a plant with homozygous genes at 95% or more of its loci.

Hulless Seed. A hulless seed is a seed that does not have a cutin layer which cements the hull (lemma and palea or glumes) to the seed. The homozygous recessive nud nud genotype results in the absence of cutin. The loose hull can be easily removed at harvest or by minimal cleaning/processing prior to consumption. This has also been referred to as naked or nude seed.

Inbred. The term inbred as used herein refers to a homozygous plant or a collection of homozygous plants.

Insect Resistance. As used herein, the term disease resistance or disease resistant is defined as the ability of plants to restrict the activities of a specified insect or pest.

Insect Tolerance. As used herein, the term disease tolerance or disease tolerant is defined as the ability of plants to endure a specified insect or pest and still perform and produce in spite thereof.

Iodine Stain—IKI—Iodine/Potassium Iodide Stock Solution for Starch Test. The stock solution of iodine stain for the starch test consists of 35 g of KI (potassium iodide) and 5 g of I (Iodine) in 500 ml of distilled water. The working solution consists of a 1:3 dilution of the stock with distilled water (1:3=one part stock and three parts water).

Iodine or Starch Test. The iodine or starch test tests for the absence or reduced levels of amylose in a plant part, most often the seed. The absence or reduced levels of amylose can be detected by cutting the nonembryo end of the seed at the dough stage and staining with a dilute iodine (IKI) stain. Amylose stains blue while amylopectin stains brown.

Lodging. As used herein, the term lodging refers to the bending or breakage of the plant stem, or the tilting over of the plant, which complicates harvest and can diminish the value of the harvested product.

Leaf Rust. Leaf rust is a fungal disease that results in orange-red pustules on the leaf surface and is caused by *Puccinia hordei*.

Net blotch. Net blotch refers to a fungal disease which appears as elongated black lesions running parallel to the leaf veins with distinctive, dark brown net-like patterns. Net blotch is caused by *Pyrenophora teres*.

Percent Identity. Percent identity, as used herein, refers to the comparison of the homozygous alleles of two barley varieties. Percent identity is determined by comparing a statistically significant number of the homozygous alleles of two developed varieties. For example, a percent identity of 90% between barley variety 1 and barley variety 2 means that the two varieties have the same allele at 90% of their loci.

Percent Similarity. Percent similarity as used herein refers to the comparison of the homozygous alleles of a barley variety such as BG-161 with another plant, and if the homozygous allele of BG-161 matches at least one of the alleles from the other plant then they are scored as similar. Percent similarity is determined by comparing a statistically significant number of loci and recording the number of loci with similar alleles as a percentage. A percent similarity of 90% between BG-161 and another plant means that BG-161 matches at least one of the alleles of the other plant at 90% of the loci.

Plant. As used herein, the term plant includes an immature or mature whole plant, including a plant from which seed, grain, or anthers have been removed. A seed or embryo that will produce the plant is also considered to be a plant.

Plant Height (Hgt). As used herein, the term plant height is defined as the average height in inches or centimeters of a group of plants, as measured from the ground level to the tip of the head, excluding awns.

Plant Parts. As used herein, the term plant parts (or reference to "a barley plant, or a part thereof") includes but is not limited to protoplasts, callus, leaves, stems, roots, root tips, anthers, pistils, seeds, grain, pericarps, embryos, pollen, ovules, cotyledons, hypocotyls, spikes, florets, awns, lemmas, shoots, tissues, petioles, cells, and meristematic cells.

Powdery Mildew. Powdery mildew refers to a fungal disease that results in white to gray powdery pustules on the leaf blade with associated yellowing and browning. Powdery mildew is caused by *Blumeria graminis* f. sp. *hordei*.

Progeny. As used herein, progeny includes an $F_1$ barley plant produced from the cross of two barley plants where at least one plant includes barley cultivar BG-161. Progeny further includes but is not limited to subsequent $F_2$, $F_3$, $F_4$, $F_5$, $F_6$, $F_7$, $F_8$, $F_9$ and $F_{10}$ generational crosses with the recurrent parental line.

Quantitative Trait Loci (QTL). Quantitative trait loci refer to genetic loci that control to some degree numerically representable traits that are usually continuously distributed.

Scab. Scab refers to a fungal disease that causes salmon-orange spore masses at the base of the glumes and on the seed. It may also cause shriveling of seed. Scab is caused by *Fusarium graminearum*.

Scald. Scald refers to a fungal disease that causes spots to develop on the leaves during cool, wet weather. The spots are oval shaped and the margins of the spots change from bluish-green to zonated brown or tan rings with bleached straw-colored centers. Scald is caused by *Rhynchosporium secalis*.

Septoria. Septoria refers to a fungal disease that appears as elongated, light brown spots on the leaves. It is caused by *Septoria passerinii*.

Shrunken endosperm: Barley seed having shrunken endosperm are long and thin or have a concave depression resulting in a reduction of the single kernel weight from 25 to 75% of normal. This characteristic is controlled by a number of single recessive genes.

Single Gene Converted (Conversion). Single gene converted (conversion) plants refers to plants which are developed by a plant breeding technique called backcrossing wherein essentially all of the desired morphological and physiological characteristics of a variety are recovered in addition to the single gene transferred into the variety via the backcrossing technique or via genetic engineering.

Smut, covered. Covered smut refers to a fungal disease in which masses of black spores replace the seed kernels on the head. A persistent membrane can be ruptured during harvest to disperse spores. Covered smut is caused by *Ustilago hordei*.

Smut, loose. Loose smut refers to a fungal disease in which masses of black spores replace the seed kernels on the head. The thin membrane that covers the spores is easily ruptured and spores disbursed by wind. Loose smut is caused by *Ustilago nuda*.

Spot blotch. Spot blotch refers to a fungal disease that appears as dark, chocolate-colored blotches forming irregular dead patches on the leaves. Spot blotch is caused by *Cochliobolus sativus*.

Stem rust. Stem rust refers to a fungal disease that produces masses of brick-red pustules on stems and leaf sheaths. Stem rust can be caused by either *Puccinia graminis* f. sp. *tritici* or *Puccinia graminis* f. sp. *secalis*.

Stripe Rust. Stripe rust refers to a fungal disease that results in light yellowish orange pustules arranged in stripes between the veins of the leaves. Stripe rust is caused by *Puccinia striiformis* f. sp. *hordei*.

Waxy Bloom. Waxy bloom is a waxy or powdery whitish to bluish coating that can be found on the surface of stems, leaves and the spike. The presence or absence of the wax is controlled genetically by a number of genes. Plant parts which do not have wax are referred to as "glossy". A synonym for presence of the wax is "glaucous".

Waxy Seed. Waxy seed refers to a seed in which the endosperm contains waxy starch granules with low amylose content. The lower amylose results in the seed having an opaque appearance. Waxy seed can be confirmed using the Iodine test.

Waxy Starch. Waxy starch in barley refers to the starch in grain that is stored in granules and has a low amylose content, ranging from 0 to 20%. Amylose content in the starch granules is genetically controlled by one or more alleles at the Wax locus on chromosome 1 (7H) which encodes the production of granule-bound starch synthase. The homozygous recessive wax wax genotype has starch granules with low amounts of amylose.

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Barley (*Hordeum vulgare* L.) is a grain that is grown worldwide with three main market classes: malt, feed and food. Most of the barley grain produced in the United States is used as an ingredient in cattle, pig, or poultry feed. Another major use for barley is malt production. Malt is used in the brewing and distilling industries to produce alcoholic beverages. Barley varieties used for producing malt are selected on the basis of characteristics such as kernel plumpness, low protein content and low beta-glucan content. Barley grain that has more than about 13.5% protein, by weight on a dry basis, or is too dark in color, is rejected by malting plants. Significant overlap between the classes can occur since barley that does not meet malting specifications can be used for feed, food, and potentially, the emerging biofuels industry.

Waxy barley is a naturally occurring variant that has recently been investigated for its potential in food and industrial processing. Barley lines having the waxy phenotype have reduced amounts of amylose starch in the seed. The waxy trait may be useful in the production of high maltose syrup from barley and in the production of flour and flakes that have health benefits.

The health promoting benefits of barley consumption have been investigated in human clinical trials. Studies have shown that individuals consuming barley that contains beta-glucan soluble fiber have significant reductions in total and LDL plasma cholesterol as well as blood pressure. In May 2006, the FDA granted a petition to allow foods containing barley with 0.75 g of beta-glucan to carry a health claim "barley lowers cholesterol when consumed as part of a healthy diet" (Federal Register 71(98):29248-29250).

Cultivated barley is a naturally self-fertilizing species, although there is a small percentage of cross-fertilization. Natural genetic and cytoplasmic male sterility is available to use in breeding and in hybrid seed production. Using all of the tools available to a breeder, it is possible to develop pure lines that are uniform in growth habit, maturity, yield, and other qualitative and quantitative characteristics. These lines can be released as inbred varieties, as inbreds for hybrid barley, or as lines to be further manipulated in the development of new lines or varieties or that incorporate proprietary genetic material.

Barley varieties may differ from each other in one or more traits and can be classified and differentiated according to the specific traits they possess. For example, there are types of barley known as two-rowed and other types known as six-rowed, referring to the number and positioning of kernels on the spike. Barley lines also can be classified as spring barley or winter barley, referring to the growth habit, or by the adherence of hulls on the seed, or by the type of starch in the seed. There are, of course, many other traits which differentiate the various lines. A discussion of breeding methods for developing barley lines and of some traits in barley can be found in Foster, A. E., *Barley*, pp. 83-125, and in Fehr, W. R., ed., *Principles of Cultivar Development* Vol. 2 Crop species. Macmillan, New York (1987).

In an embodiment, the invention is directed to barley cultivar BG-161, its seeds, plants, and hybrids. BG-161 is a waxy starch, hulless, two-row barley variety that has shrunken endosperm created by crossing "BZ594-27e" and "Prowashonupana". BZ594-27e is a waxy endosperm, hulless spring barley developed by WestBred from the cross of "Baronesse/Merlin". Prowashonupana is a two-rowed, hulless, waxy endosperm spring barley with seed that has shrunken endosperm developed by Montana State University. Following the cross described above, $F_1$, $F_2$ and $F_3$ bulk populations were grown in research nurseries. $F_3$ heads that had shrunken endosperm seed were selected and planted as spike rows. Selected (agronomic traits) rows were advanced to yield trials and purification head rows. One uniform spike row from this grow-out, having waxy endosperm, shrunken endosperm and hulless seed was selected on the basis of good agronomic characteristics. BG-161 will be used as high beta-glucan grain for use as a human food and food ingredient.

BG-161 is a short awned, two-row, medium-maturing, semi-dwarf variety adapted to the intermountain areas of the Pacific Northwest. Selection for agronomic performance and high beta-glucan content resulted in plants that produce acceptable yield and very high levels of cell wall beta-glucan soluble fiber which has been found to be a powerful fat, cholesterol, glucose and immune regulator of the human GI tract.

BG-161 has a slightly waxy stem and leaves. The sheath and leaf blades do not have pubescence. The spike of BG-161 is two-rowed, has a straight neck, a closed collar, is slightly waxy, strap shaped, mid-dense and erect at maturity. The spike has a many hairs on the rachis edge. The glumes of BG-161 are approximately one-half of the lemma length, have a band of long hairs, and have rough awns that are equal to the length of the glume. The lemma has short awns that are rough. The base of the lemma has a depression and the rachilla hairs are short. BG-161 seed are hulless with white aleurone, are midlong to long and have shrunken endosperm.

The BG-161 variety has shown uniformity and stability, and is described in the following variety description information in Table 1. It has been self-pollinated a sufficient number of generations to ensure uniformity.

TABLE 1

Physiological and Morphological Characteristics for Barley BG-161

Plant:

Growth Habit: Spring
Spike: Two-row
Juvenile Growth Habit: Erect
Plant Tillering: Intermediate
Maturity (50% flowering): Medium; averages 60 days after planting; this is similar to Prowashonupana
Plant Height: Semi-dwarf, averages 55 cm; 12.0 cm shorter than Prowashonupana
Stem Color at Maturity: White
Stem Strength: Strong
Neck Shape: Straight
Collar Shape: Closed
Leaves:

Coleoptile Color: Green
Basal Leaf Sheath Pubescence at Seedling Stage: Absent
Basal Leaf Sheath Color: White TABLE 1-continued Physiological and Morphological Characteristics for Barley BG-161

Leaf Color at Boot: Green
Flag Leaf at Boot: Erect, curled, slightly waxy bloom
Pubescence on Leaf (first leaf below flag leaf) Blade: No
Pubescence on Leaf (first leaf below flag leaf) Sheath: No
Auricle Color: White
Pubescence on Auricle: Absent
Spike:

Exsertion: Slight
Shape: Strap
Density: Mid-dense
Position at Maturity: Erect
Length of Spike: Long
Waxy Bloom: Slightly waxy
Hairiness of Rachis Edge: Covered
Rachilla Hairs: Short
Lateral Florets: None
Awns:

Awns: Straight
Length: Short
Surface: Rough
Glumes:

Length: One-half of lemma
Hairiness: Confined to bands
Length of Hairs: Long
Glume Awn Surface: Rough
Glume Awn Length Relative to Glume Length: Equal
Hull/Kernel:

Hull Type (Lemma/Palea Adherence): Hulless
Hairs on Ventral Furrow: Absent
Shape of Base: Depression
Kernel Aleurone Color: Colorless
Kernel Length: Mid-long to long
Average 1,000 Kernel Weight: 32 g, similar to the variety Prowashonupana
Diseases:

Stem Rust, *Septoria*, Net and Spot blotch: Not tested
Smut, loose and covered: Susceptible
Other Characteristics:

BG-161 has waxy starch which can be identified by the opaqueness of the seed and by a brown stain when the seed is cut in half at dough stage and the iodine or starch test is performed.
Normal non-waxy seed (25% amylose) stains blue. BG-161 seed have a shrunken endosperm.

The invention encompasses BG-161 progeny with the same or greater yield or test weight as BG-161, the same or shorter plant height, and the same or greater resistance to smut, stem rust, *Septoria*, net and spot blotch of BG-161. The expression of these traits may be measured by a side by side phenotypic comparison, with differences and similarities determined at a 5% significance level.

In an embodiment, the BG-161 barley plants of the invention are inbred. Inbred BG-161 barley plants can be produced by planting the seeds of the inbred barley plant designated BG-161 and growing the resulting barley plants under self-pollinating or sib-pollinating conditions with adequate isolation, using standard techniques well known to an artisan skilled in the agricultural arts. Recurrent selection may be utilized in this embodiment. In other embodiments, the invention may comprise barley plants produced via single-seed descent or bulk breeding.

In a particular embodiment, the present invention provides a method of producing an inbred barley plant derived from the barley variety designated BG-161, the method comprising the steps of: (a) preparing a progeny plant derived from barley variety BG-161, wherein said preparing comprises crossing a plant of the barley variety BG-161 with a second barley plant; (b) crossing the progeny plant with itself or a second plant to produce a seed of a progeny plant of a subsequent generation; (c) growing a progeny plant of a subsequent generation from said seed of a progeny plant of a subsequent generation and crossing the progeny plant of a subsequent generation with itself or a second plant; and (d) repeating the steps for an additional 3 to 10 generations to produce an inbred barley plant derived from the barley variety BG-161. In the method, it may be desirable to select particular plants resulting from step (c) for continued crossing according to steps (b) and (c). By selecting plants having one or more desirable traits, an inbred barley plant derived from the barley variety BG-161 may be obtained which possesses some or essentially all of the desirable traits of barley variety BG-161 as well as potentially other selected traits. In a particular embodiment, the invention comprises an elite BG-161 barley parent plant or line.

In yet another embodiment, the invention is directed to parts of the BG-161 barley plant. Any part of the BG-161 barley plant is contemplated in this embodiment. In an embodiment, the plant part may comprise pollen obtained from a BG-161 barley plant. In still another embodiment, the invention comprises seed of the BG-161 barley plant. Seeds can be harvested from a BG-161 plant using standard, well-known procedures.

In an embodiment, the seeds are inbred BG-161 seeds. Inbred barley seed of the invention may be provided as an essentially homogeneous population of inbred barley seed of the variety designated BG-161. Essentially homogeneous populations of inbred seed may be free from substantial numbers of seeds that are significantly different on a genetic basis. In an embodiment of the present invention, inbred seed may form greater than about 97% of the total seed. In an embodiment, the population of inbred barley seed of the invention may be essentially free from hybrid seed. In some embodiments, the inbred seed population may be grown separately from any hybrid population to provide an essentially homogeneous population of inbred barley plants designated BG-161.

In yet another embodiment of the invention, a tissue culture of regenerable cells of a plant of the variety designated BG-161 is provided. The regenerable cells in such tissue cultures may be derived from head, awn, leaf, pollen, embryo, cotyledon, hypocotyl, seed, spike, pericarp, meristematic cell, protoplast, root, root tip, pistil, anther, floret, shoot, stem and/or callus. Still further, the present invention provides barley plants regenerated from the tissue cultures of the invention. Means for preparing and maintaining plant tissue cultures are well known in the art.

In an embodiment, the tissue culture may be capable of regenerating plants capable of expressing essentially all of the physiological and morphological characteristics of the BG-161 variety, and of regenerating plants having substantially the same genotype as other plants of the BG-161 variety. Still further, the present invention provides barley plants regenerated from the tissue cultures of the invention, the plants having all or essentially all of the physiological and morphological characteristics of the variety designated BG-161.

In a particular embodiment, the invention relates to a BG-161 barley hybrid. A barley hybrid is the cross of two inbred lines, each of which may have one or more desirable characteristics lacked by the other and/or which complement the other. As used herein, crossing can include selfing, back-crossing, crossing to another or the same inbred, and/or crossing to populations. Thus, in another embodiment, the invention is directed to a method of producing a hybrid barley plant. The method may involve crossing barley cultivar BG-161 with another barley cultivar. More particularly, the barley cultivar of the invention could be used in crosses with other, different, barley plants to produce first generation ($F_1$) barley hybrid seeds and plants with superior characteristics.

In an embodiment, barley variety BG-161 may be crossed with another variety of barley, such as an elite variety. The $F_1$ seed derived from this cross could be grown to form a homogeneous population. The $F_1$ seed would contain one set of the alleles from variety BG-161 and one set of the alleles from the other barley variety. The $F_1$ genome would be made-up of 50% variety BG-161 and 50% of the other elite variety. The $F_1$ seed would be grown and allowed to self, thereby forming $F_2$ seed. On average, the $F_2$ seed would have derived 50% of its alleles from variety BG-161 and 50% from the other barley variety, but various individual plants from the population would have a much greater percentage of their alleles derived from BG-161 (Wang J. and R. Bernardo, 2000, *Crop Sci.* 40:659-665 and Bernardo, R. and A. L. Kahler, 2001, *Theor. Appl. Genet.* 102:986-992). The $F_2$ seed would be grown and selection of plants would be made based on visual observation and/or measurement of traits. The BG-161-derived progeny that exhibit one or more of the desired BG-161-derived traits would be selected and each plant would be harvested separately. This $F_3$ seed from each plant would be grown in individual rows and allowed to self. Then selected rows or plants from the rows would be harvested and threshed individually. The selections would again be based on visual observation and/or measurements for desirable traits of the plants, such as one or more of the desirable BG-161-derived traits. The process of growing and selection would be repeated any number of times until a homozygous BG-161-derived barley plant is obtained. The homozygous BG-161-derived barley plant would contain desirable traits derived from barley variety BG-161, some of which may not have been expressed by the other original barley variety to which barley variety BG-161 was crossed and some of which may have been expressed by both barley varieties, but now would be at a level equal to or greater than the level expressed in barley variety BG-161. The homozygous BG-161-derived barley plants would have, on average, 50% of their genes derived from barley variety BG-161, but various individual plants from the population would have a much greater percentage of their alleles derived from BG-161. The breeding process, of crossing, selfing, and selection may be repeated to produce another population of BG-161-derived barley plants with, on average, 25% of their genes derived from barley variety BG-161, but various individual plants from the population would have a much greater percentage of their alleles derived from BG-161. Another embodiment of the invention is a homozygous BG-161-derived barley plant that has received BG-161-derived traits.

The previous example can be modified in numerous ways. For instance, selection may or may not occur at every selfing generation, selection may occur before or after the actual self-pollination process occurs, or individual selections may be made by harvesting individual spikes, plants, rows or plots at any point during the breeding process described. In addition, double haploid breeding methods may be used at any step in the process. The population of plants produced at each and any generation of selfing is also an embodiment of the invention, and each such population would consist of plants containing approximately 50% of its genes from barley variety BG-161, 25% of its genes from barley variety BG-161 in the second cycle of crossing, selfing, and selection, 12.5% of its genes from barley variety BG-161 in the third cycle of crossing, selfing, and selection, and so on.

Another embodiment of this invention is a method of developing a backcross conversion BG-161 barley plant that involves the repeated backcrossing to barley variety BG-161. The number of backcrosses made may be 2, 3, 4, 5, 6 or greater, and the specific number of backcrosses used will depend upon the genetics of the donor parent and whether molecular markers are utilized in the backcrossing program. Using backcrossing methods, one of ordinary skill in the art can develop individual plants and populations of plants that retain at least 70%, 75%, 79%, 80%, 81%, 82%, 83%, 84%, 85%, 86%, 87%, 88%, 89%, 90%, 91%, 92%, 93%, 94%, 95%, 96%, 97%, 98%, or 99% of the genetic profile of barley variety BG-161. The percentage of the genetics retained in the backcross conversion may be measured by either pedigree analysis or through the use of genetic techniques such as molecular markers or electrophoresis. In pedigree analysis, 50% of the starting germplasm on average would be passed to the progeny line after one cross to another line, 75% after backcrossing once, 87.5% after backcrossing twice, and so on. Molecular markers could also be used to confirm and/or determine the recurrent parent used. The backcross conversion developed from this method may be similar to BG-161 for the results listed in Table 1. Such similarity may be measured by a side-by-side phenotypic comparison, with differences and similarities determined at a 5% significance level. Any such comparison should be made in environmental conditions that account for the trait being transferred. For example, herbicide should not be applied in the phenotypic comparison of herbicide resistant backcross conversion of BG-161 to a herbicide resistant non-backcross conversion of BG-161.

Another embodiment of the invention is an essentially derived variety of BG-161. As determined by the UPOV Convention, essentially derived varieties may be obtained, for example, by the selection of a natural or induced mutant, or of a somaclonal variant, the selection of a variant individual from plants of the initial variety, backcrossing, or transformation by genetic engineering. An essentially derived variety of BG-161 is further defined as one whose production requires the repeated use of variety BG-161 or is predominately derived from variety BG-161. International Convention for the Protection of New Varieties of Plants, as amended on Mar. 19, 1991, Chapter V, Article 14, Section 5(c).

In another embodiment, the method may involve the creation of variants by mutagenesis or transformation of barley cultivar BG-161. All plants produced using barley cultivar BG-161 as at least one parent are considered within the scope of this invention.

In another aspect, the present invention provides for single or multiple gene converted plants of barley cultivar BG-161. The transferred gene(s) may be a dominant or recessive allele. The transferred gene(s) may confer such traits as herbicide tolerance or resistance, insect tolerance or resistance, tolerance or resistance for bacterial, fungal, or viral disease, male fertility, male sterility, enhanced nutritional quality, modified fatty acid metabolism, modified carbohydrate metabolism, modified seed yield, modified protein percent, modified beta-glucan percent, modified lodging resistance, modified lipoxygenase, beta-glucanase and/or polyphenol oxidase content and/or activity, and/or industrial usage. The gene may be a naturally occurring barley gene or a transgene introduced through genetic engineering techniques.

Any method for plant transformation known in the art or yet to be discovered may be utilized in the present invention. The invention comprises transgenic methods including, but not limited to, expression vectors introduced into plant tissues using a direct gene transfer method such as microprojectile-mediated delivery, DNA injection, electroporation and the like. In an embodiment, expression vectors may be introduced into plant tissues by using either microprojectile-mediated delivery with a biolistic device or by using *Agrobacterium*-mediated transformation. Transformed plants obtained with the protoplasm of barley cultivar BG-161 are intended to be within the scope of this invention.

Various genetic elements can be introduced into the plant genome using transformation. These elements include but are not limited to genes, coding sequences, inducible, constitutive, and tissue specific promoters, enhancing sequences and signal and targeting sequences.

In an embodiment of the invention, a genetic trait which has been engineered into a barley BG-161 plant using transformation techniques could then be moved into another line using traditional breeding techniques that are well known in the plant breeding arts. For example, a backcrossing approach could be used to move a transgene from a transformed barley BG-161 plant to an elite barley variety and the resulting progeny would comprise a transgene.

Likewise, in an embodiment of the present invention, agronomic genes can be expressed in transformed BG-161 plants. More particularly, plants can be genetically engineered to express various phenotypes of agronomic interest. Through the transformation of BG-161 plants, the expression of genes can be modulated to enhance disease tolerance or resistance, insect tolerance or resistance, herbicide tolerance or resistance, water stress tolerance, agronomic traits, and/or grain quality traits. Transformation can also be used to insert DNA sequences which control or help control male-sterility. DNA sequences native to barley as well as non-native DNA sequences can be transformed into barley and used to modulate levels of native or non-native proteins. Anti-sense technology, various promoters, targeting sequences, enhancing sequences, and other DNA sequences can be inserted into the BG-161 barley genome for the purpose of modulating the expression of proteins. Exemplary genes that can be inserted into the BG-161 barley genome as part of the present invention include, but are not limited to, those categorized below.

1. Genes that Confer Tolerance or Resistance to Pests or Disease:

(A) Plant disease resistance genes. Plant defenses are often activated by specific interaction between the product of a disease resistance gene (R) in the plant and the product of a corresponding avirulence (Avr) gene in the pathogen. In an embodiment of the invention, a BG-161 plant variety can be transformed with a cloned resistance gene to engineer plants that are tolerant or resistant to specific pathogen strains. See, for example, Jones, et al., *Science* 266: 789 (1994) (cloning of the tomato Cf-9 gene for resistance to *Cladosporium fulvum*); Martin, et al., Science 262: 1432 (1993) (tomato Pto gene for resistance to *Pseudomonas syringae* pv. tomato encodes a protein kinase); Mindrinos, et al., *Cell* 78: 1089 (1994) (Arabidopsis RSP2 gene for resistance to *Pseudomonas syringae*); McDowell & Woffenden, (2003) *Trends Biotechnol.* 21(4): 178-83 and Toyoda, et al., (2002) *Transgenic Res.* 11(6):567-82.

*Fusarium* head blight along with deoxynivalenol both produced by the pathogen *Fusarium graminearum* Schwabe have caused devastating losses in barley production. Genes expressing proteins with antifungal action can be used as transgenes to prevent *Fusarium* head blight. Various classes of proteins have been identified. Examples include endochitinases, exochitinases, glucanases, thionins, thaumatin-like proteins, osmotins, ribosome inactivating proteins, flavonoids, and lactoferricin. During infection with *Fusarium graminearum*, deoxynivalenol is produced. There is evidence that production of deoxynivalenol increases the virulence of the disease. Genes with properties for detoxification of deoxynivalenol (Adam and Lemmens, In *International Congress on Molecular Plant-Microbe Interactions*, 1996; McCormick, et al. *Appl. Environ. Micro.* 65:5252-5256, 1999) have been engineered for use in barley. A synthetic peptide that competes with deoxynivalenol has been identified (Yuan, et al., *Appl. Environ. Micro.* 65:3279-3286 (1999)). Changing the ribosomes of the host so that they have reduced affinity for deoxynivalenol has also been used to reduce the virulence of *Fusarium graminearum*.

Genes used to help reduce *Fusarium* head blight include, but are not limited to, Tri101 (*Fusarium*), PDR5 (yeast), tlp-1(oat), tlp-2(oat), leaf tlp-1 (wheat), tlp (rice), tlp-4 (oat), endochitinase, exochitinase, glucanase (*Fusarium*), permatin (oat), seed hordothionin (barley), alpha-thionin (wheat), acid glucanase (alfalfa), chitinase (barley and rice), class beta II-1,3-glucanase (barley), PR5/tlp (*Arabidopsis*), zeamatin (maize), type 1 RIP (barley), NPR1 (*Arabidopsis*), lactoferrin (mammal), oxalyl-CoA-decarboxylase (bacterium), IAP (baculovirus), ced-9 (*C. elegans*), and glucanase (rice and barley).

(B) A gene conferring tolerance or resistance to a pest, such as Hessian fly, wheat stem soft fly, cereal leaf beetle, and/or green bug. For example the H9, H10, and H21 genes.

(C) A gene conferring resistance to such diseases as barley rusts, *Septoria tritici, Septoria nodorum*, powdery mildew, *Helminthosporium* diseases, smuts, bunts, *Fusarium* diseases, bacterial diseases, and viral diseases.

(D) A *Bacillus thuringiensis* protein, a derivative thereof or a synthetic polypeptide modeled thereon. See, for example, Geiser, et al., *Gene* 48: 109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other examples of *Bacillus thuringiensis* transgenes being genetically engineered are given in the following patents and patent applications: U.S. Pat. Nos. 5,188,960; 5,689,052; 5,880,275; PCT App. Nos. WO 91/14778; WO 99/31248; WO 01/12731; WO 99/24581; WO 97/40162; and U.S. patent application Ser. Nos. 10/032,717; 10/414,637; and 10/606,320.

(E) An insect-specific hormone or pheromone such as an ecdysteroid or juvenile hormone, a variant thereof, a mimetic based thereon, or an antagonist or agonist thereof. See, for example, the disclosure by Hammock, et al., *Nature* 344: 458 (1990), of baculovirus expression of cloned juvenile hormone esterase, an inactivator of juvenile hormone.

(F) An insect-specific peptide which, upon expression, disrupts the physiology of the affected pest. For example, see the disclosures of Regan, *J. Biol. Chem.* 269: 9 (1994) (expression cloning yields DNA coding for insect diuretic hormone receptor); Pratt, et al., *Biochem. Biophys. Res. Comm.* 163: 1243 (1989) (an allostatin is identified in *Diploptera punctata*); Chattopadhyay, et al. (2004) *Critical Reviews in Microbiology* 30 (1): 33-54 2004; Zjawiony (2004) *J Nat Prod* 67 (2): 300-310; Carlini & Grossi-de-Sa (2002) *Toxicon,* 40 (11):1515-1539; Ussuf, et al. (2001) *Curr Sci.* 80 (7): 847-853; and Vasconcelos & Oliveira (2004) *Toxicon* 44 (4): 385-403. See also U.S. Pat. No. 5,266,317 to Tomalski, et al., who disclose genes encoding insect-specific toxins.

(G) An enzyme responsible for a hyperaccumulation of a monoterpene, a sesquiterpene, a steroid, hydroxamic acid, a phenylpropanoid derivative or another non-protein molecule with insecticidal activity.

(H) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT App. No. WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also Kramer, et al., *Insect Biochem, Molec, Biol,* 23: 691 (1993), who teach the nucleotide sequence of a cDNA encoding tobacco hornworm chitinase, and Kawalleck, et al., *Plant Molec. Biol.* 21: 673 (1993), who provide the nucleotide sequence of the parsley ubi4-2 polyubiquitin gene, U.S. patent application Ser. Nos. 10/389,432; 10/692,367; and U.S. Pat. No. 6,563,020.

(I) A molecule that stimulates signal transduction. For example, see the disclosure by Botella, et al., Plant Molec. Biol. 24: 757 (1994), of nucleotide sequences for mung bean calmodulin cDNA clones, and Griess, et al., *Plant Physiol.* 104: 1467 (1994), who provide the nucleotide sequence of a maize calmodulin cDNA clone.

(J) A hydrophobic moment peptide. See PCT App. No. WO 95/16776 and U.S. Pat. No. 5,580,852 (disclosure of peptide derivatives of Tachyplesin which inhibit fungal plant pathogens) and PCT App. No. WO 95/18855 and U.S. Pat. No. 5,607,914) (teaches synthetic antimicrobial peptides that confer disease resistance).

(K) A membrane permease, a channel former or a channel blocker. For example, see the disclosure by Jaynes, et al., *Plant Sci.* 89: 43 (1993), of heterologous expression of a cecropin-beta lytic peptide analog to render transgenic tobacco plants resistant to *Pseudomonas solanacearum*.

(L) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy, et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus, Id.

(M) An insect-specific antibody or an immunotoxin derived therefrom. Thus, an antibody targeted to a critical metabolic function in the insect gut would inactivate an affected enzyme, killing the insect. Cf. Taylor, et al, Abstract #497, *Seventh International Symposium on Molecular Plant-Microbe Interactions* (Edinburgh, Scotland, 1994) (enzymatic inactivation in transgenic tobacco via production of single-chain antibody fragments).

(N) A virus-specific antibody. See, for example, Tavladoraki, et al., *Nature* 366: 469 (1993), who show that transgenic plants expressing recombinant antibody genes are protected from virus attack.

(O) A developmental-arrestive protein produced in nature by a pathogen or a parasite. Thus, fungal endo-alpha-1,4-D-polygalacturonases facilitate fungal colonization and plant nutrient release by solubilizing plant cell wall homo-alpha-1,4-D-galacturonase. See Lamb, et al., *Bio/Technology* 10: 1436 (1992). The cloning and characterization of a gene which encodes a bean endo-poly-galacturonase-inhibiting protein is described by Toubart, et al., Plant J. 2: 367 (1992).

(P) A developmental-arrestive protein produced in nature by a plant. For example, Logemann, et al., *Bio/Technology* 10: 305 (1992), have shown that transgenic plants expressing the barley ribosome-inactivating gene have an increased resistance to fungal disease.

(O) Genes involved in the Systemic Acquired Resistance response and/or the pathogenesis-related genes. Briggs, S., *Current Biology,* 5(2):128-131 (1995), Pieterse & Van Loon (2004) *Curr. Opin. Plant Bio.* 7(4):456-64 and Somssich (2003) *Cell* 11 3(7):81 5-6.

(R) Antifungal genes (Cornelissen and Melchers, *Pl. Physiol.* 101:709-712, (1993) and Parijs, et al., *Planta* 183: 258-264, (1991) and Bushnell, et al., *Can. J. of Plant Path.* 20(2):137-149 (1998). Also see U.S. patent application Ser. No. 09/950,933.

(S) Detoxification genes, such as for fumonisin, beauvericin, moniliformin and zearalenone and their structurally related derivatives, For example, see U.S. Pat. No. 5,792,931.

(T) Cystatin and cysteine proteinase inhibitors, See U.S. patent application Ser. No. 10/947,979.

(U) Defensin genes. See PCT App. No. WO 03/000863 and U.S. patent application Ser. No. 10/178,213.

(V) Genes conferring resistance to nematodes. See PCT App. No. WO 03/033651 and Urwin et. al., *Planta* 204:472-479 (1998), Williamson (1999) *Curr Opin Plant Bio.* 2(4): 327-31.

2. Genes that Confer Tolerance or Resistance to an Herbicide:

(A) Acetohydroxy acid synthase. Acetohydroxy acid synthase, which has been found to make plants that express this enzyme resistant to multiple types of herbicides, has been introduced into a variety of plants (see, e.g., Hattori, et al. (1995) *Mol Gen Genet.* 246:419).

Other genes that confer tolerance to herbicides include: a gene encoding a chimeric protein of rat cytochrome P4507A1 and yeast NADPH-cytochrome P450 oxidoreductase (Shiota, et al. (1994) *Plant Physiol Plant Physiol* 106:17), genes for glutathione reductase and superoxide dismutase (Aono, et al. (1995) *Plant Cell Physiol* 36:1687, and genes for various phosphotransferases (Datta, et al. (1992) *Plant Mol Biol* 20:619).

(B) An herbicide that inhibits the growing point or meristem, such as an imidazolinone or a sulfonylurea. Exemplary genes in this category code for mutant ALS and AHAS enzyme as described, for example, by Lee, et al., *EMBO J.* 7: 1241 (1988), and Miki, et al., *Theor. Appl. Genet.* 80: 449 (1990), respectively. See also U.S. Pat. Nos. 5,605,011; 5,013,659; 5,141,870; 5,767,361; 5,731,180; 5,304,732; 4,761,373; 5,331,107; 5,928,937; and 5,378,824; and PCT App. No. WO 96/33270.

(C) Glyphosate (resistance imparted by mutant 5-enolpyruvl-3-phosphoshikimate synthase (EPSP) and aroA genes, respectively) and other phosphono compounds such as glufosinate (phosphinothricin acetyl transferase (PAT) and *Streptomyces hygroscopicus* PAT (bar) genes), and pyridinoxy or phenoxy proprionic acids and cycloshexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al. also describes genes encoding EPSPS enzymes. See also U.S. Pat. Nos. 6,566,587; 6,338,961; 6,248,876; 6,040,497; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; Re. 36,449; RE 37,287 E; 5,491,288; EP Pat. Pub. No. EP1173580; PCT App. No. WO 01/66704; EP Pat. Pub. Nos. EP1173581; and EP1173582. Glyphosate resistance is also imparted to plants that express a gene that encodes a glyphosate oxido-reductase enzyme as described more fully in U.S. Pat. Nos. 5,776,760 and 5,463,175. In addition glyphosate resistance can be imparted to plants by the over-expression of genes encoding glyphosate N-acetyltransferase. See, for example, U.S. patent application Ser. Nos. 10/46227; 10/427,692; and 10/427,692. A DNA molecule encoding a mutant aroA gene can be obtained under ATCC accession No. 39256, and the nucleotide sequence of the mutant gene is disclosed in U.S. Pat. No. 4,769,061 to Comai. European Patent Application No. 0 333 033 to Kumada, et al. and U.S. Pat. No. 4,975,374 to Goodman, et al. disclose nucleotide sequences of glutamine synthetase genes which confer resistance to herbicides such as L-phosphinothricin. The nucleotide sequence of a PAT gene is provided in European Patent No. 0 242 246 and 0 242 236 to Leemans, et al. De Greet et al., *Bio/Technology* 7: 61 (1989), describe the production of transgenic plants that express chimeric bar genes coding for PAT activity. See also U.S. Pat. Nos. 5,969,213; 5,489,520; 5,550,318; 5,874,265; 5,919,675; 5,561,236; 5,648,477; 5,646,024; 6,177,616; and U.S. Pat. No. 5,879,903. Exemplary genes conferring resistance to phenoxy proprionic acids and cycloshexones, such as sethoxydim and haloxyfop, are the Acc1-S1, Acc1-S2 and Acc1-S3 genes described by Marshall, et al., *Theor. Appl. Genet.* 83: 435 (1992).

(D) An herbicide that inhibits photosynthesis, such as a triazine (psbA and gs+genes) and a benzonitrile (nitrilase gene). Przibilla, et al., *Plant Cell* 3: 169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes, et al., *Biochem. J.* 285:173 (1992).

(E) Protoporphyrinogen oxidase (protox). Protox is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282, 837; 5,767,373; and PCT App. No. WO 01/12825.

3. Genes that Confer or Improve Grain Quality:

(A) Genes that alter fatty acids. For example, fatty acids may be altered by: (1) down-regulation of stearyl-ACP desaturase to increase stearic acid content of the plant, by for example, transforming a plant with a nucleic acid encoding an anti-sense of stearyl-ACP desaturase (see Knultzon, et al., *Proc. Natl. Acad. Sci. USA* 89: 2624 (1992) and PCT App. No. WO 99/64579 (Genes for Desaturases to Alter Lipid Profiles in Corn); (2) elevating oleic acid via FAD-2 gene modification and/or decreasing linolenic acid via FAD-3 gene modification (see U.S. Pat. Nos. 6,063,947; 6,323,392; 6,372,965 and PCT App. No. WO 93/11245); (3) altering conjugated linolenic or linoleic acid content, such as in PCT App. No. WO 01/12800; and/or (4) altering LEC1, AGP, Dek1, Superal1, mi1ps, and various Ipa genes such as Ipa1, Ipa3, hpt or hggt (see PCT App. Nos. WO 02/42424; WO 98/22604; WO 03/011015; U.S. Pat. Nos. 6,423,886; 6,197,561; 6,825, 397; U.S. Pat. App. Nos. 2003/0079247; 2003/0204870; PCT App. Nos. WO 02/057439; WO 03/011015; and Rivera-Madrid, R., et al. *Proc. Natl. Acad. Sci.* 92:5620-5624 (1995)).

(B) Genes that alter phosphorus content. For example, phosphorus content may be altered by: (1) introduction of a phytase-encoding gene would enhance breakdown of phytate, adding more free phosphate to the transformed plant (see Van Hartingsveldt, et al., *Gene* 127: 87 (1993) (nucleotide sequence of an *Aspergillus niger* phytase gene)); (2) up-regulation of a gene that reduces phytate content.

(C) Genes that alter carbohydrates. This can be effected, for example, by altering a gene for an enzyme that affects the branching pattern of starch or a gene altering thioredoxin (See U.S. Pat. No. 6,531,648). See Shiroza, et al., *J. Bacteriol.* 170: 810 (1988) (nucleotide sequence of *Streptococcus mutans* fructosyltransferase gene), Steinmetz, et al., *Mol. Gen. Genet.* 200: 220 (1985) (nucleotide sequence of *Bacillus subtilis* levansucrase gene), Pen, et al., Bio/Technology 10: 292 (1992) (production of transgenic plants that express *Bacillus licheniformis* alpha-amylase), Elliot, et al., *Plant Molec. Biol.* 21: 515 (1993) (nucleotide sequences of tomato invertase genes), Sogaard, et al., *J. Biol. Chem.* 268: 22480 (1993) (site-directed mutagenesis of barley alpha-amylase gene), and Fisher, et al., *Plant Physiol.* 102: 1045 (1993) (maize endosperm starch branching enzyme II), PCT App. No. WO 99/10498 (improved digestibility and/or starch extraction through modification of UDP-D-xylose 4-epimerase, Fragile 1 and 2, Refl, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683; U.S. Pat. App. No. 2004/0034886; and PCT App. No. WO 00/68393 involving the manipulation of antioxidant levels through alteration of a phytl prenyl transferase (ppt), PCT App. No. WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds); U.S. Pat. No. 6,080,913 (binary methods of increasing accumulation of essential amino acids in seeds); U.S. Pat. No. 5,990,389 (high lysine); PCT App, No. WO 99/40209 (alteration of amino acid compositions in seeds); WO 99/29882 (methods for altering amino acid content of proteins); U.S. Pat. No. 5,850,016 (alteration of amino acid compositions in seeds); PCT App. No. WO 98/20133 (proteins with enhanced levels of essential amino acids); U.S. Pat. No. 5,885,802 (high methionine); (high threonine); U.S. Pat. No. 6,664,445 (plant amino acid biosynthetic enzymes); U.S. Pat. No. 6,459,019 (increased lysine and threonine); U.S. Pat. No. 6,441,274 (plant tryptophan synthase beta subunit); U.S. Pat. No. 6,346,403 (methionine metabolic enzymes); U.S. Pat. No. 5,939,599 (high sulfur); U.S. Pat. No. 5,912,414 (increased methionine); PCT App. Nos. WO 98/56935 (plant amino acid biosynthetic enzymes); WO 98/45458 (engineered seed protein having higher percentage of essential amino acids); WO 98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants); PCT App. Nos. WO 96/01905 (increased threonine); WO 95/15392 (increased lysine); U.S. Pat. App. Nos. 2003/0163838; 2003/0150014; 2004/

0068767; U.S. Pat. No. 6,803,498; PCT App. Nos. WO 01/79516 and WO 00/09706 (Ces A: cellulose synthase); U.S. Pat. No. 6,194,638 (hemicellulose); U.S. Pat. No. 6,399,859; U.S. Pat. App. No. 2004/0025203 (UDPGdH); and U.S. Pat. No. 6,194,638 (RGP).

4. Genes that Control Male Sterility:

There are several methods of conferring genetic male sterility available, such as multiple mutant genes at separate locations within the genome that confer male sterility, as disclosed in U.S. Pat. Nos. 4,654,465 and 4,727,219 to Brar, et al. and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed Fertility is restored by inducing, or turning "on", the promoter, which in turn allows the gene that confers male fertility to be transcribed.

(A) Introduction of a deacetylase gene under the control of a tapetum-specific promoter and with the application of the chemical N-Ac-PPT (PCT App. No. WO 01/29237).

(B) Introduction of various stamen-specific promoters (PCT App. Nos. WO 92/13956 and WO 92/13957).

(C) Introduction of the barnase and the barstar gene (Paul, et al. *Plant Mol. Biol.* 19:611-622, 1992).

For additional examples of nuclear male and female sterility systems and genes, see also U.S. Pat. Nos. 5,859,341; 6,297,426; 5,478,369; 5,824,524; 5,850,014; and 6,265,640.

5. Genes that Create a Site for Site-Specific DNA Integration:

Genes that create a site for site-specific DNA integration include FRT sites that may be used in the FLP/FRT system and/or Lox sites that may be used in the Cre/Loxp system. For example, see Lyznik, et al., Site-Specific Recombination for Genetic Engineering in Plants, *Plant Cell Rep* (2003) 21:925-932 and PCT App. No. WO 99/25821. Other systems that may be used include the Gin recombinase of phage Mu, the Pin recombinase of *E. coli*, and the R/RS system of the pSRi plasmid.

6. Genes that Affect Abiotic Stress Resistance:

(A) Genes that include, but are not limited to, flowering, ear and seed development, enhancement of nitrogen utilization efficiency, altered nitrogen responsiveness, drought resistance or tolerance, cold resistance or tolerance, and salt resistance or tolerance and increased yield under stress. For example, see: PCT App. No. WO 00/73475 where water use efficiency is altered through alteration of malate; U.S. Pat. Nos. 5,892,009; 5,965,705; 5,929,305; 5,891,859; 6,417,428; 6,664,446; 6,706,866; 6,717,034; 6,801,104; PCT App. Nos. WO 00/060089; WO 01/026459; WO 01/035725; WO 2001/034726; WO 2001/035727; WO 2001/036444; WO 2001/036597; WO 2001/036598; WO 2002/015675; WO 2002/017430; WO 2002/077185; WO 2002/079403; WO 2003/013227; WO 2003/013228; WO 2003/014327; WO 2004/031349; WO 2004/076638; WO 98/09521; and WO 99/38977 describing genes, including CBF genes and transcription factors effective in mitigating the negative effects of freezing, high salinity, and drought on plants, as well as conferring other positive effects on plant phenotype; U.S. Pat. App. No. 2004/0148654 and PCT App. No. WO 01/36596 where abscisic acid is altered in plants resulting in improved plant phenotype such as increased yield and/or increased tolerance to abiotic stress; PCT App. Nos. WO 2000/006341 and WO 04/090143; U.S. patent application Ser. Nos. 10/817,483 and 09/545,334, where cytokinin expression is modified resulting in plants with increased stress tolerance, such as drought tolerance, and/or increased yield. Also see PCT App. Nos. WO 02/02776; WO 2003/052063; Japan Pat. No. JP2002281975; U.S. Pat. No. 6,084,153; PCT App. No. WO 01/64898; U.S. Pat. Nos. 6,177,275; and 6,107,547 (enhancement of nitrogen utilization and altered nitrogen responsiveness). For ethylene alteration, see U.S. Pat. App. No. 2004/0128719; 2003/0166197; and PCT App. No. WO 2000/32761. For plant transcription factors or transcriptional regulators of abiotic stress, see e.g. U.S. Pat. App. Nos. 2004/0098764 and 2004/0078852.

(B) Improved tolerance to water stress from drought or high salt water condition. The HVA1 protein belongs to the group 3 LEA proteins that include other members such as wheat pMA2005 (Curry, et al., 1991; Curry and Walker-Simmons, 1993), cotton D-7 (Baker, et al., 1988), carrot Dc3 (Seffens, et al., 1990), and rape pLEA76 (Harada, et al., 1989). These proteins are characterized by 11-mer tandem repeats of amino acid domains which may form a probable amphophilic alpha-helical structure that presents a hydrophilic surface with a hydrophobic stripe (Baker, et al., 1988; Dure, et al., 1988; Dure, 1993). The barley HVA1 gene and the wheat pMA2005 gene (Curry, et al., 1991; Curry and Walker-Simmons, 1993) are highly similar at both the nucleotide level and predicted amino acid level. These two monocot genes are closely related to the cotton D-7 gene (Baker, et al., 1988) and carrot Dc3 gene (Seffens, et al., 1990) with which they share a similar structural gene organization (Straub, et al., 1994). There is, therefore, a correlation between LEA gene expression or LEA protein accumulation with stress tolerance in a number of plants. For example, in severely dehydrated wheat seedlings, the accumulation of high levels of group 3 LEA proteins was correlated with tissue dehydration tolerance (Ried and Walker-Simmons, 1993). Studies on several Indica varieties of rice showed that the levels of group 2 LEA proteins (also known as dehydrins) and group 3 LEA proteins in roots were significantly higher in salt-tolerant varieties compared with sensitive varieties (Moons, et al., 1995). The barley HVA1 gene was transformed into wheat. Transformed wheat plants showed increased tolerance to water stress (Sivamani, E., et al. *Plant Science* (2000), V.155 pl-9 and U.S. Pat. No. 5,981,842).

(C) Improved water stress tolerance through increased mannitol levels via the bacterial mannitol-1-phosphate dehydrogenase gene. To produce a plant with a genetic basis for coping with water deficit, Tarczynski, et al. (*Proc. Natl. Acad. Sci. USA*, 89, 2600 (1992); PCT App. No. WO 92/19731) introduced the bacterial mannitol-1-phosphate dehydrogenase gene, mtlD, into tobacco cells via *Agrobacterium*-mediated transformation. Root and leaf tissues from transgenic plants regenerated from these transformed tobacco cells contained up to 100 mM mannitol. Control plants contained no detectable mannitol. To determine whether the transgenic tobacco plants exhibited increased tolerance to water deficit, Tarczynski, et al. compared the growth of transgenic plants to that of untransformed control plants in the presence of 250 mM NaCl. After 30 days of exposure to 250 mM NaCl, transgenic plants exhibited decreased weight loss and increased height relative to their untransformed counterparts. The authors concluded that the presence of mannitol in these transformed tobacco plants contributed to water deficit tolerance at the cellular level. See also U.S. Pat. No. 5,780,709 and Pct. App. No. WO 92/19731.

Other genes and transcription factors that affect plant growth and agronomic traits such as yield, flowering, plant growth and/or plant structure, can be introduced or introgressed into plants, see e.g. PCT App. Nos. WO 97/49811 (LHY); WO 98/56918 (ESD4); WO 97/10339; U.S. Pat. No. 6,573,430 (TFL); U.S. Pat. No. 6,713,663 (FT); PCT App. Nos. WO 96/14414 (CON); WO 96/38560; WO 01/21822 (VRN1); WO 00/44918 (VRN2); WO 99/49064 (GI); WO 00/46358 (FRI); WO 97/29123; U.S. Pat. Nos. 6,794,560; 6,307,126 (GAI); PCT App. Nos. WO 99/09174 (D8 and Rht); WO 04/076638; and WO 04/031349 (transcription factors).

7. Genes that Confer Agronomic Enhancements, Nutritional Enhancements, or Industrial Enhancements:

Genes that alter enzyme activity for improved disease resistance and/or improved plant or grain quality may be introduced or introgressed into plants. For example, lipoxygenase levels can be altered to improve disease resistance (Steiner-Lange, S., et al. 2003. *MPMI.* 16(10):893-902 (differential defense reactions in leaf tissues of barley in response to infection by *Rhynchosporium secalis* and to treatment with a fungal avirulence gene product)) and/or to improve the quality of the grain, resulting in improved flavor for beer, cereal and other food products made from the grain (Douma, A., et al. 2003; U.S. Pat. No. 6,660,915). Another enzyme whose activity can be altered is beta-glucanase for improved plant and/or grain quality (Han, F., et al. *Theor. Appl. Genet.* 91:921-927 (1995) (mapping of beta-glucan content and beta-glucanase activity loci in barley grain and malt); Han, F., et al. *Theor. Appl. Genet.* 95:903-910 (1997) (fine structure mapping and tagging major malting quality QTL in barley); Jensen, L. G., et al. *Proc. Natl. Acad. Sci. U.S.A.* 93(8):3487-3491 (1996) (transgenic barley expressing a protein-engineered, thermostable (1,3-1,4)-beta-glucanase during germination). Yet another enzyme whose activity can be altered is polyphenol oxidase for improved plant and/or grain quality (Cahoon, R. 2004; U.S. Pat. App. No. 2004/0214201).

Further embodiments of the invention are the treatment of BG-161 with a mutagen and the plant produced by mutagenesis of BG-161. Information about mutagens and mutagenizing seeds or pollen is presented in the IAEA's *Manual on Mutation Breeding* (IAEA, 1977).

A further embodiment of the invention is a backcross conversion of barley variety BG-161. A backcross conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to, nutritional enhancements, industrial enhancements, disease resistance, insect resistance, herbicide resistance, agronomic enhancements, grain quality enhancement, waxy starch, breeding enhancements, seed production enhancements, and male sterility. Descriptions of some of the cytoplasmic male sterility genes, nuclear male sterility genes, chemical hybridizing agents, male fertility restoration genes, and methods of using the aforementioned are discussed in *Hybrid Wheat* by K. A. Lucken (pp. 444-452 *Wheat and Wheat Improvement*, ed. Heyne, 1987). Examples of genes for other traits include: leaf rust resistance genes (Lr series such as Lr1, Lr10, Lr21, Lr22, Lr22a, Lr32, Lr37, Lr41, Lr42, and Lr43), *Fusarium* head blight-resistance genes (QFhs.ndsu-3B and QFhs.ndsu-2A), powdery mildew resistance genes (Pm21), common bunt resistance genes (Bt-10), and wheat streak mosaic virus resistance gene (Wsm1), russian wheat aphid resistance genes (Dn series such as Dn1, Dn2, Dn4, Dn5), black stem rust resistance genes (Sr38), yellow rust resistance genes (Yr series such as Yr1, YrSD, Yrsu, Yr17, Yr15, YrH52), aluminum tolerance genes (Alt(BH)), dwarf genes (Rht), vernalization genes (Vm), hessian fly resistance genes (H9, H10, H21, H29), grain color genes (R/r), glyphosate resistance genes (EPSPS), glufosinate genes (bar, pat) and water stress tolerance genes (Hva1, mtID). The trait of interest is transferred from the donor parent to the recurrent parent, in this case, the barley plant disclosed herein. Single gene traits may result from either the transfer of a dominant allele or a recessive allele. Selection of progeny containing the trait of interest is done by direct selection for a trait associated with a dominant allele. Selection of progeny for a trait that is transferred via a recessive allele requires growing and selfing the first backcross to determine which plants carry the recessive alleles. Recessive traits may require additional progeny testing in successive backcross generations to determine the presence of the gene of interest.

Molecular markers including techniques such as Starch Gel Electrophoresis, Isozyme Electrophoresis, Restriction Fragment Length Polymorphisms, Randomly Amplified Polymorphic DNAs, Arbitrarily Primed Polymerase Chain Reaction, DNA Amplification Fingerprinting, Sequence Characterized Amplified Regions, Amplified Fragment Length Polymorphisms, Simple Sequence Repeats, and Single Nucleotide Polymorphisms may be used in plant breeding methods. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program (Openshaw et al. Marker-assisted Selection in Backcross Breeding. *In: Proceedings Symposium of the Analysis of Molecular Marker Data*, 5-6 Aug. 1994, pp. 41-43. Crop Science Society of America, Corvallis, Oreg.). The use of molecular markers in the selection process is often called Genetic Marker Enhanced Selection.

The following examples describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples.

EXAMPLE 1

Barley cultivar BG-161 was tested for agronomic performance and beta-glucan content in small plots in six environments in Montana and Idaho in 2010. Comparisons between BG-161 and the commercially available food barley cultivars BG 46e and Prowashonupana are shown in Table 2.

In Table 2, column one shows the cultivar, column two shows the yield in bushels/acre (bu/a), column three shows the test weight in pounds/bushel (lbs/bu), column four shows heading date in Bozeman, Mont. as days after July 1, column five shows the plant height in centimeters (cm), and column six shows the beta-glucan content of the grain as a percent dry weight basis (% dwb). The data shows that BG-161 has a consistently shorter height and higher yield than these commercially available cultivars with similar beta-glucan content.

TABLE 2

| Cultivar | YIELD bu/a | TEST WEIGHT lbs/bu | HEADING Days after July 1 | PLANT HEIGHT cm | BETA-GLUCAN FIBER % dwb |
| --- | --- | --- | --- | --- | --- |
| BG-161 | 42.7 | 51 | 20 | 57 | 14.4 |
| BG 46e | 34.0 | 53 | 23 | 81 | 14.6 |
| Prowashonupana | 33.2 | 51 | 21 | 65 | 15.1 |
| No. Locations | 6 | 7 | 2 | 2 | 3 |

EXAMPLE 2

Barley cultivar BG-161 was tested for agronomic performance in small plots in six environments in Montana and Idaho in 2011. Comparisons between BG-161 and the commercially available food barley cultivars BG 46e and Prowashonupana are shown in Table 3.

In Table 3, column one shows the cultivar, column two shows the yield in bushels/acre (bu/a), column three shows the test weight in pounds/bushel (lbs/bu), column four shows heading date in Bozeman, Mont. as days after July 1, column five shows the plant height in centimeters (cm), and column six shows the beta-glucan content of the grain as a percent dry weight basis (% dwb). The data shows that BG-161 has a consistently shorter height and higher yield than these commercially available cultivars with similar beta-glucan content.

TABLE 3

| VARIETY | YIELD bu/a | TEST WEIGHT lbs/bu | HEADING Days after July 1 | PLANT HEIGHT cm | BETA-GLUCAN FIBER % dwb |
| --- | --- | --- | --- | --- | --- |
| BG-161 | 42.7 | 51 | 20 | 57 | 14.4 |
| BG 46e | 34.0 | 53 | 23 | 81 | 14.6 |
| Prowashonupana | 33.2 | 51 | 21 | 65 | 15.1 |
| No. Sites | 6 | 7 | 2 | 2 | 3 |

DEPOSIT INFORMATION

A deposit of the barley seed of this invention is maintained by WestBred LLC, 81 Timberline Dr., Bozeman, Mont. 59718. Access to this deposit will be available during the pendency of this application to persons determined by the Commissioner of Patents and Trademarks to be entitled thereto under 37 CFR §1.14 and 35 U.S.C §122. Upon allowance of any claims in this application, all restrictions on the availability to the public of the variety will be irrevocably removed by affording access to a deposit of at least 2,500 seeds of the same cultivar with the American Type Culture Collection, Manassas, Va. or National Collections of Industrial, Food and Marine Bacteria (NCIMB), 23 St Machar Drive, Aberdeen, Scotland, AB24 3RY, United Kingdom.

All references cited in this specification, including without limitation, all papers, publications, patents, patent applications, presentations, texts, reports, manuscripts, brochures, books, internet postings, journal articles, and/or periodicals are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and is not intended to limit the invention so further described in such appended claims. Therefore, the spirit and scope of the appended claims should not be limited to the description of the versions contained therein.

What is claimed is:

1. A seed of barley cultivar BG-161, a representative sample of seed of which was deposited under ATCC Accession No. PTA-121758.

2. A barley plant, or a part thereof, produced by growing the seed of claim 1.

3. A tissue culture produced from protoplasts or cells from the plant of claim 2, wherein said protoplasts or cells of the tissue culture are produced from a plant part selected from the group consisting of head, awn, leaf, pollen, embryo, cotyledon, hypocotyl, seed, spike, pericarp, meristematic cell, root, root tip, pistil, anther, floret, shoot, stem and callus.

4. A barley plant regenerated from the tissue culture of claim 3, wherein the plant has essentially all of the morphological and physiological characteristics of barley cultivar BG-161.

5. A method for producing a barley seed comprising crossing two barley plants and harvesting the resultant barley seed, wherein at least one barley plant is the barley plant of claim 2.

6. A barley seed produced by the method of claim 5.

7. A barley plant, or a part thereof, produced by growing said seed of claim 6.

8. A method of producing an herbicide tolerant barley plant wherein the method comprises transforming the barley plant of claim 2 with a transgene wherein the transgene confers tolerance to an herbicide selected from the group consisting of imidazolinone, sulfonylurea, glyphosate, glufosinate, phenoxy proprionic acid, cyclohexane, L-phosphinothricin, triazine and benzonitrile.

9. An herbicide tolerant barley plant produced by the method of claim 8.

10. A method of producing a pest or insect resistant barley plant wherein the method comprises transforming the barley plant of claim 2 with a transgene that confers pest or insect resistance.

11. A pest or insect resistant barley plant produced by the method of claim 10.

12. The barley plant of claim 11, wherein the transgene encodes a *Bacillus thuringiensis* endotoxin.

13. A method of producing a disease resistant barley plant wherein the method comprises transforming the barley plant of claim 2 with a transgene that confers disease resistance.

14. A disease resistant barley plant produced by the method of claim 13.

15. A method of producing a barley plant with modified fatty acid metabolism, modified carbohydrate metabolism or modified protein metabolism wherein the method comprises transforming the barley plant of claim 2 with a transgene encoding a protein selected from the group consisting of modified glutenins, gliadins, phytase, lipoxygenase, beta-glucanase, polyphenol oxidase, fructosyltransferase, levansucrase, α-amylase, invertase and starch branching enzyme or encoding an antisense of stearyl-ACP desaturase.

16. A barley plant having modified fatty acid metabolism, modified carbohydrate metabolism or modified protein metabolism produced by the method of claim 15.

17. A method of introducing a desired trait into barley cultivar BG-161 wherein the method comprises:
(a) crossing a BG-161 plant, wherein a representative sample of seed was deposited under ATCC Accession No. PTA-121758, with a plant of another barley cultivar that comprises a desired trait to produce progeny plants wherein the desired trait is selected from the group consisting of male sterility, herbicide resistance, insect resistance, modified fatty acid metabolism, modified carbohydrate metabolism, modified phytic acid metabolism, modified waxy starch content, modified protein content, increased stress to water tolerance and resistance to bacterial disease, fungal disease or viral disease;
(b) selecting one or more progeny plants that have the desired trait to produce selected progeny plants;
(c) crossing the selected progeny plants with the BG-161 plants to produce backcross progeny plants;
(d) selecting for backcross progeny plants that have the desired trait and essentially all of the physiological and morphological characteristics of barley cultivar BG-161 listed in Table 1 to produce selected backcross progeny plants; and
(e) repeating the crossing the selected progeny step and selecting for backcross progeny step two or more times in succession to produce selected third or higher backcross progeny plants that comprise the desired trait and essentially all of the physiological and morphological characteristics of barley cultivar BG-161 listed in Table 1.

18. A barley plant produced by the method of claim 17, wherein the plant has the desired trait.

19. The barley plant of claim 18, wherein the desired trait is herbicide tolerance and the tolerance is conferred to an herbicide selected from the group consisting of imidazolinone, sulfonylurea, glyphosate, glufosinate, phenoxy proprionic acid, cyclohexane, L-phosphinothricin, triazine and benzonitrile.

20. The barley plant of claim 18, wherein the desired trait is insect resistance and the insect resistance is conferred by a transgene encoding a *Bacillus thuringiensis* endotoxin.

21. The barley plant of claim 18, wherein the desired trait is modified fatty acid metabolism, modified carbohydrate metabolism or modified protein metabolism and said desired trait is conferred by a nucleic acid encoding a protein selected from the group consisting of modified glutenins, gliadins, phytase, lipoxygenase, beta-glucanase, polyphenol oxidase, fructosyltransferase, levansucrase, α-amylase, invertase and starch branching enzyme or encoding an antisense of stearyl-ACP desaturase.

22. The barley plant of claim 20, wherein the desired trait is male sterility and the trait is conferred by a nucleic acid molecule that confers male sterility.

* * * * *

UNITED STATES PATENT AND TRADEMARK OFFICE
CERTIFICATE OF CORRECTION

PATENT NO. : 9,040,783 B2
APPLICATION NO. : 13/644224
DATED : May 26, 2015
INVENTOR(S) : Dale R. Clark It is certified that error appears in the above-identified patent and that said Letters Patent is hereby corrected as shown below:

In the claims,

Column 17, Line 43 "recombinase of E. coli, and the R/RS system of the pSRi" should read -- recombinase of E. coli, and the R/RS system of the pSR1. --.

Signed and Sealed this
Twenty-second Day of March, 2016

Michelle K. Lee
*Director of the United States Patent and Trademark Office*